United States Patent [19]
Matsumura et al.

[11] Patent Number: 6,077,966
[45] Date of Patent: Jun. 20, 2000

[54] PREPARATION OF WATER-SOLUBLE ORGANIC SILICON COMPOUNDS

[75] Inventors: Kazuyuki Matsumura; Mitsuo Asai; Shoji Ichinohe, all of Usui-gun, Japan

[73] Assignee: Shin-Etsu Chemical Co., Ltd., Tokyo, Japan

[21] Appl. No.: 08/709,036

[22] Filed: Sep. 6, 1996

[30] Foreign Application Priority Data

Sep. 8, 1995 [JP] Japan ................................ 7-256893

[51] Int. Cl.$^7$ ..................................................... C07F 7/10
[52] U.S. Cl. ......................... 556/425; 556/413; 427/387; 427/393.6; 427/397
[58] Field of Search ................................. 556/413, 425; 427/387, 397, 393.6

[56] References Cited

U.S. PATENT DOCUMENTS

| | | | |
|---|---|---|---|
| 5,077,421 | 12/1991 | Selvig | 556/425 |
| 5,087,715 | 2/1992 | Snow | 556/413 |
| 5,276,123 | 1/1994 | King et al. | 556/425 X |
| 5,567,752 | 10/1996 | Stein et al. | 556/425 X |

*Primary Examiner*—Paul F. Shaver
*Attorney, Agent, or Firm*—Millen, White, Zelane & Branigan, P.C.

[57] ABSTRACT

Water-soluble organic silicon compounds are prepared by effecting co-hydrolysis of (A) 1–30 parts of an alkyltrialkoxysilane of $R^1Si(OR^2)_3$ or a partial hydrolyzate thereof, (B) 70–90 parts of an alkoxy-containing siloxane of $R^3{}_a(OR^2)_b SiO_{(4-a-b)/2}$, and (C) 1–20 parts of an amino-containing alkoxysilane of $R^4R^5NR^6$—$SiR^7{}_n(OR^2)_{3-n}$ or a partial hydrolyzate thereof in the presence of an organic or inorganic acid. $R^1$ is a $C_7$–$C_{18}$ alkyl group, $R^2$ is a $C_1$–$C_4$ alkyl group, $R^3$ is a $C_1$–$C_6$ alkyl group, $R^4$ and $R^5$ are a hydrogen atom, $C_1$–$C_{15}$ alkyl or aminoalkyl group, $R^6$ is a divalent $C_1$–$C_{18}$ hydrocarbon group, and $R^7$ is a $C_1$–$C_4$ alkyl group. Letters a and b are $0.75 \leq a \leq 1.5$, $0.2 \leq b \leq 2$, and $0.95 < a+b < 3.4$. These water-soluble organic silicon compounds are fully water soluble and shelf stable and can be used as an agent for preventing porous materials from water absorption simply after dilution with water. Porous materials are coated or impregnated with the compounds so that they are given excellent water repellency and water absorption-preventing effect.

20 Claims, No Drawings ic silicon compounds">

PREPARATION OF WATER-SOLUBLE ORGANIC SILICON COMPOUNDS

BACKGROUND OF THE INVENTION

1. Field of the Invention

This invention relates to a method for preparing a water-soluble organic silicon compound which is useful as an aqueous agent for preventing water absorption of porous materials and a primer for various paints and finishers.

2. Prior Art

For the purpose of preventing water absorption of porous materials, especially porous building and construction materials, it is a common practice to coat or impregnate porous materials with solutions of silicone, acrylic, urethane, ester and fat resins or monomers followed by drying. Among these, silicone systems are widely used, and water absorption preventing silicone agents of the solvent dilution type constitute the mainstream.

Since the solvent dilution type involves risks of fire, explosion and poisoning, and from the aspects of global environment protection and resource utilization, it is desired to develop a water-absorption preventing agent free of a solvent, especially a high performance aqueous water-absorption preventing agent.

Aqueous water-absorption preventing agents known thus far include long-lasting emulsions of alkyltrialkoxysilanes emulsified in water as disclosed in Japanese Patent Application Kokai (JP-A) Nos. 292089/1989, 156164/1993, and 221748/1993. These emulsions use alkoxysilanes characterized by very slow hydrolysis reaction. When the emulsions are applied to objective materials, impregnation is effective, but silanes volatilize at the material surface, losing surface water-repellency and allowing water wetting, staining and pop-up due to freezing. Long-lasting action is not expected. Milky white outer appearance is also a problem.

Aside from the emulsion type, a uniform aqueous solution type is disclosed in JP-A 162553/1986 and 249588/1992. These compositions form clear mixtures when diluted with water. When the composition of JP-A 162553/1986 is diluted with water, shelf stability is low in that quick polymerization reaction takes place. It must be used within a day after dilution. This is impractical. The quick polymerization reaction also leads to a higher molecular weight so that material impregnation becomes less efficient, sometimes leaving wetting spots on the material surface.

The composition of JP-A 249588/1992 contains a water-soluble amino-containing coupling agent and an alkyltrialkoxysilane having a short carbon chain. It is shelf stable, but less water repellent because only the lower alkyl group is a water repellent component. The high loading of the amino-containing coupling agent can leave wet color art materials and cause serious yellowing of wood.

Therefore, the above-mentioned water-absorption preventing agents are not considered satisfactory in performance.

SUMMARY OF THE INVENTION

An object of the present invention is to provide a method for preparing a water-soluble organic silicon compound which is effectively impregnable in porous materials to impart water absorption-preventing and water repellent functions thereto and thus useful as an aqueous water-absorption preventing agent.

The present invention provides a method for preparing a water-soluble organic silicon compound by effecting co-hydrolysis of components (A), (B) and (C) in the presence of an organic or inorganic acid. Component (A) is 1 to 30 parts by weight of an alkyltrialkoxysilane of the following general formula (1):

$$R^1Si(OR^2)_3 \qquad (1)$$

wherein $R^1$ is an alkyl group having 7 to 18 carbon atoms and $R^2$ is an alkyl group having 1 to 4 carbon atoms, or a partial hydrolyzate thereof. Component (B) is 70 to 90 parts by weight of an alkoxy-containing siloxane of the following general formula (2):

$$R^3_a(OR^2)_b SiO_{(4-a-b)/2} \qquad (2)$$

wherein $R^2$ is as defined above, $R^3$ is an alkyl group having 1 to 6 carbon atoms, letters a and b are positive numbers satisfying $0.75 \leq a \leq 1.5$, $0.2 \leq b \leq 2$, and $0.95 < a+b < 3.4$. Component (C) is 1 to 20 parts by weight of an amino-containing alkoxysilane of the following general formula (3):

$$R^4R^5NR^6-SiR^7_n(OR^2)_{3-n} \qquad (3)$$

wherein $R^2$ is as defined above, $R^4$ and $R^5$ are independently selected from the group consisting of a hydrogen atom, alkyl and aminoalkyl groups having 1 to 15 carbon atoms, $R^6$ is a divalent hydrocarbon group having 1 to 18 carbon atoms, and $R^7$ is an alkyl group having 1 to 4 carbon atoms, or a partial hydrolyzate thereof. Letter n is 0 or 1. Preferably, the co-hydrolysis step is carried out by effecting hydrolysis of an alkyltrialkoxysilane of formula (1) or a partial hydrolyzate thereof in the presence of an organic or inorganic acid, mixing the resulting hydrolyzate with an alkoxy-containing siloxane of formula (2), effecting hydrolysis of the mixture in the presence of an organic or inorganic acid, and finally reacting the resulting hydrolyzates with an amino-containing alkoxysilane of formula (3) or a partial hydrolyzate thereof. The thus obtained organic silicon compound itself is water soluble and forms a homogeneous solution when dissolved in water so that it can be used simply by diluting with water. In addition, the compound is shelf stable even after dilution with water. The compound well penetrates into porous materials to improve long-term water repellency and restrain volatilization at the material surface. The compound is thus effective for preventing water wetting, staining, and pop-up due to freezing. When wood and other organic materials are treated with the compound, yellowing is minimized. Accordingly, the organic silicon compound according to the invention is effectively impregnable in porous materials to impart water absorption-preventing and water repellent functions thereto.

DETAILED DESCRIPTION OF THE INVENTION

According to the present invention, a water-soluble organic silicon compound is prepared by effecting co-hydrolysis of components (A), (B) and (C) in the presence of an organic or inorganic acid. Component (A) is an alkyltrialkoxysilane of the following general formula (1) or a partial hydrolyzate thereof.

$$R^1Si(OR^2)_3 \qquad (1)$$

$R^1$ is an alkyl group having 7 to 18 carbon atoms and $R^2$ is an alkyl group having 1 to 4 carbon atoms.

In the alkyltrialkoxysilane of formula (1), $R^1$ is an alkyl group having 7 to 18 carbon atoms, preferably 7 to 10 carbon atoms, typically a $C_7$–$C_{10}$ alkyl group. With less than 7 carbon atoms for $R^1$, water repellency is weak and polymerization takes place too rapidly. With more than 18 carbon atoms for $R^1$, preparation is difficult. The hydrocarbon group represented by $R^1$ may be normal, branched or cyclic while its examples are $C_7H_{15}$, $C_8H_{17}$, $C_9H_{19}$, and $C_{10}H_{21}$.

$R^2$ is an alkyl group having 1 to 4 carbon atoms, for example, methyl, ethyl, n-propyl, isopropyl, n-butyl and isobutyl groups, with the methyl and ethyl groups being preferred.

Several illustrative, non-limiting, examples of the alkyltrialkoxysilane of formula (1) are given below.

$C_8H_{17}Si(OCH_3)_3$, $C_8H_{17}Si(OC_2H_5)_3$, $C_8H_{17}Si(OCH(CH_3)_2)_3$,
$C_{10}H_{21}Si(OCH_3)_3$, $C_{10}H_{21}Si(OC_2H_5)_3$, $C_{10}H_{21}Si(OCH(CH_3)_2)_3$,
$C_{12}H_{25}Si(OCH_3)_3$, $C_{12}H_{25}Si(OC_2H_5)_3$, $C_{12}H_{25}Si(OCH(CH_3)_2)_3$,
$C_{14}H_{29}Si(OCH_3)_3$, $C_{14}H_{29}Si(OC_2H_5)_3$, $C_{14}H_{29}Si(OCH(CH_3)_2)_3$,
$C_{16}H_{33}Si(OCH_3)_3$, $C_{16}H_{33}Si(OC_2H_5)_3$, $C_{16}H_{33}Si(OCH(CH_3)_2)_3$,
$C_{18}H_{37}Si(OCH_3)_3$, $C_{18}H_{37}Si(OC_2H_5)_3$, $C_{18}H_{37}Si(OCH(CH_3)_2)_3$.

Among them, $C_8H_{17}Si(OCH_3)_3$, $C_8H_{17}Si(OC_2H_5)_3$, $C_{10}H_{21}Si(OCH_3)_3$ and $C_{10}H_{21}Si(OC_2H_5)_3$ are preferred.

An oligomer resulting from partial hydrolysis and condensation of the silane of formula (1) may also be used as component (A) as is well known in the art. Such a partial hydrolyzate should preferably have 2 to 10 silicon atoms, especially 2 to 4 silicon atoms.

In the practice of the invention, silanes of formula (1) may be used alone or in admixture of two or more. A partial hydrolyzate of mixed silanes is also acceptable.

Component (B) is an alkoxy-containing siloxane of the following general formula (2).

$$R^3{}_a(OR^2)_b SiO_{(4-a-b)/2} \quad (2)$$

$R^2$ is as defined above, $R^3$ is an alkyl group having 1 to 6 carbon atoms, letters a and b are positive numbers satisfying $0.75 \leq a \leq 1.5$, $0.2 \leq b \leq 2$, and $0.95 < a+b < 3.4$.

In formula (2), $R^2$ is as defined in formula (1) and its examples are the same. $R^3$ is an alkyl group having 1 to 6 carbon atoms. Examples include methyl, ethyl, n-propyl, isopropyl, n-butyl, isobutyl, t-butyl, n-pentyl, isopentyl, neopentyl, t-pentyl, and hexyl groups, with the methyl and ethyl groups being desirable.

The alkoxy-containing siloxane of formula (2) can be synthesized by conventional processes. Advantageously, it is synthesized by reacting an alkyltrichlorosilane having 1 to 6 carbon atoms or a mixture thereof with methanol or ethanol in water.

Preferably the alkoxy-containing siloxane of formula (2) has 2 to 6 silicon atoms, especially 2 to 4 silicon atoms. The siloxane preferably has a viscosity of up to 300 mm²/sec. at 25° C., especially 1 to 100 mm²/sec. at 25° C.

Component (C) is an amino-containing alkoxysilane of the following general formula (3) or a partial hydrolyzate thereof.

$$R^4R^5NR^6-SiR^7{}_n(OR^2)_{3-n} \quad (3)$$

$R^2$ is as defined above, each of $R^4$ and $R^5$ is a hydrogen atom, alkyl group having 1 to 15 carbon atoms or aminoalkyl group having 1 to 15 carbon atoms, $R^6$ is a divalent hydrocarbon group having 1 to 18 carbon atoms, and $R^7$ is an alkyl group having 1 to 4 carbon atoms. Letter n is 0 or 1.

Examples of the group represented by $R^4$ and $R^5$ include methyl, ethyl, propyl, butyl, aminomethyl, aminoethyl, aminopropyl, and aminobutyl groups. Examples of the group represented by $R^6$ are alkylene groups including methylene, ethylene, propylene, and butylene groups. Examples of the group represented by $R^7$ include methyl, ethyl, propyl, and butyl groups.

Several illustrative, non-limiting, examples of the amino-containing alkoxysilane of formula (3) are given below.

$H_2N(CH_2)_2Si(OCH_3)_3$, $H_2N(CH_2)_2Si(OCH_2CH_3)_3$,
$H_2N(CH_2)_3Si(OCH_3)_3$, $H_2N(CH_2)_3Si(OCH_2CH_3)_3$,
$CH_3NH(CH_2)_3Si(OCH_3)_3$, $CH_3NH(CH_2)_3Si(OCH_2CH_3)_3$,
$CH_3NH(CH_2)_5Si(OCH_3)_3$, $CH_3NH(CH_2)_5Si(OCH_2CH_3)_3$,
$H_2N(CH_2)_2NH(CH_2)_3Si(OCH_3)_3$, $H_2N(CH_2)_2NH(CH_2)_3Si(OCH_2CH_3)_3$,
$CH_3NH(CH_2)_2NH(CH_2)_3Si(OCH_3)_3$, $CH_3NH(CH_2)_2NH(CH_2)_3Si(OCH_2CH_3)_3$,
$C_4H_9NH(CH_2)_2NH(CH_2)_3Si(OCH_3)_3$, $C_4H_9NH(CH_2)_2NH(CH_2)_3Si(OCH_2CH_3)_3$,
$H_2N(CH_2)_2SiCH_3(OCH_3)_2$, $H_2N(CH_2)_2SiCH_3(OCH_2CH_3)_2$,
$H_2N(CH_2)_3SiCH_3(OCH_3)_2$, $H_2N(CH_2)_3SiCH_3(OCH_2CH_3)_2$,
$CH_3NH(CH_2)_3SiCH_3(OCH_3)_2$, $CH_3NH(CH_2)_3SiCH_3(OCH_2CH_3)_2$,
$CH_3NH(CH_2)_5SiCH_3(OCH_3)_2$, $CH_3NH(CH_2)_5SiCH_3(OCH_2CH_3)_2$,
$H_2N(CH_2)_2NH(CH_2)_3SiCH_3(OCH_3)_2$, $H_2N(CH_2)_2NH(CH_2)_3SiCH_3(OCH_2CH_3)_2$,
$CH_3NH(CH_2)_2NH(CH_2)_3SiCH_3(OCH_3)_2$,
$CH_3NH(CH_2)_2NH(CH_2)_3SiCH_3(OCH_2CH_3)_2$,
$C_4H_9NH(CH_2)_2NH(CH_2)_3SiCH_3(OCH_3)_2$,
$C_4H_9NH(CH_2)_2NH(CH_2)_3SiCH_3(OCH_2CH_3)_2$

Preferred among these are N-(2-aminoethyl)-3-aminopropyltrimethoxysilane, N-(2-aminoethyl)-3-aminopropyl-methyldimethoxysilane, and 3-aminopropyltrimethoxysilane.

Components (A), (B), and (C) are used in such a proportion that there are present 1 to 30 parts, preferably 5 to 20 parts of component (A), 70 to 90 parts, preferably 70 to 80 parts of component (B), and 1 to 20 parts, preferably 10 to 20 parts of component (C). Note that all parts are parts by weight. Outside this range, less amounts of component (A) lead to weaker water repellency whereas excessive amounts of component (A) would result in an organic silicon compound which forms an unstable aqueous solution. Less amounts of component (B) would adversely affect durable water repellency whereas excessive amounts of component (B) would lead to weaker water repellency. Less amounts of component (C) would adversely affect water solubility whereas excessive amounts of component (C) would lead to weaker water repellency and allow for wetting spots.

According to the present invention, a water-soluble organic silicon compound is prepared from components (A), (B), and (C) by effecting co-hydrolysis of these components in the presence of an organic or inorganic acid. Preferably it is prepared by effecting hydrolysis of component (A) in the presence of an organic or inorganic acid, mixing the resulting hydrolyzate with component (B), adding water to the mixture in the presence of an organic or inorganic acid for effecting further hydrolysis, and finally reacting the resulting hydrolyzates with component (C). Then a more stable silicon compound is obtained.

The organic and inorganic acids used in hydrolysis of component (A) include hydrochloric acid, sulfuric acid, s methanesulfonic acid, formic acid, acetic acid, propionic acid, citric acid, oxalic acid, maleic acid and mixtures thereof, with the acetic acid and propionic acid being preferred. The acid is preferably used in an amount of 2 to 40 parts by weight, more preferably 3 to 15 parts by weight per 100 parts by weight of component (A).

Hydrolysis is preferably carried out after component (A) is diluted with a suitable solvent. The solvent used herein is preferably an alcoholic solvent, for example, methanol, ethanol, isopropyl alcohol, and tert-butyl alcohol. The solvent is preferably used in an amount of 50 to 300 parts by weight, more preferably 70 to 200 parts by weight per 100 parts by weight of component (A). Less than 50 parts of the solvent would allow for fast condensation whereas more than 300 parts of the solvent would retard hydrolysis.

For hydrolysis, water is preferably added to component (A) in an amount of 1 to 4 mol, especially 2 to 3.5 mol per mol of component (A). With less than 1 mol of water, more alkoxy groups would be left whereas more than 4 mol of water would allow for fast condensation.

Preferred reaction conditions for hydrolysis of component (A) to proceed include a temperature of 10 to 40° C., especially 20 to 30° C. and a time of 1 to 3 hours.

The thus obtained hydrolyzate of component (A) is mixed with component (B). At this point, component (B) may have been diluted with a solvent. The solvent used herein is an alcoholic solvent as mentioned above. The amount of solvent used is preferably 0 to 300 parts by weight, more preferably 50 to 200 parts by weight per 100 parts by weight of component (B).

Mixing of the hydrolyzate of component (A) with component (B) is preferably effected at a temperature of 10 to 40° C., especially 20 to 30° C. for 1 to 3 hours.

Upon hydrolysis of the mixture of the hydrolyzate of component (A) and component (B), an organic or inorganic acid is desirably added simultaneously with water. The organic or inorganic acid used herein may be the same as used in hydrolysis of component (A).

Preferably the amount of organic or inorganic acid used is 2 to 40 parts, especially 3 to 15 parts by weight per 100 parts by weight of component (B). The amount of water added is preferably 0.5 to 1.5 mol, especially 0.6 to 1 mol per mol of component (B). Less than 0.5 mol of water would, be too small for hydrolysis to take place, resulting in a final product which is poor in water solubility and shelf stability of-its aqueous solution. More than 1.5 mol of water would allow for fast condensation, resulting in a final product which is less impregnable in porous materials.

Preferred reaction conditions for this second stage hydrolysis to proceed include a temperature of 10 to 40° C., especially 20 to 30° C. and a time of 1 to 3 hours.

Finally the hydrolyzate of component (A) and the hydrolyzate of component (B) are reacted with component (C). Preferred reaction conditions include a temperature of 60 to 100° C. and a time of 1 to 3 hours. At the end of reaction, the reaction solution is heated above the boiling point of the solvent for distilling off the solvent. The reaction product (the resulting water-soluble organic silicon compound) prepared by the above-mentioned method desirably has a weight average molecular weight of 500 to 5,000, especially 1,000 to 2,000.

The organic silicon compound of the invention is a co-hydrolysis/condensation product of components (A), (B), and (C) prepared by the above-mentioned method. Since component (B) is a major component, the product has a moderately controlled molecular weight, good penetrability to porous materials, and durable water repellency. Controlled volatilization at the material surface restrains water wetting, staining and pop-up due to freezing. A dilution of the organic silicon compound with water is improved in shelf stability because polymerization reaction in water is suppressed. If an organic silicon compound is similarly prepared from components (A) and (C) without component (B), then polymerization proceeds too much so that the compound is less soluble in water and poor in outer appearance. When component (A) having less than 7 carbon atoms in $R^1$ is used, the resulting compound is acceptable in water solubility and outer appearance, but poor in water repellency and durable water repellency.

Component (C) serves to impart water solubility. Silicon compounds free of component (C) are insoluble in water. Since component (B) is a major component, the amount of component (C) used can be reduced, which is helpful in minimizing yellowing.

The water-soluble organic silicon compounds of the invention are applicable to substrates such as inorganic porous materials, wood and wood composites as a water-absorption preventing agent. The compounds are also useful as a primer for various paints and finishers.

Exemplary porous materials are porous building and construction materials, for example, materials based on inorganic substances such as as-cast concrete, lightweight concrete, precast concrete, aerated lightweight concrete (ALC), mortar, joint mortar, asbestos cement boards, pulp cement boards, wood fiber cement boards, glass fiber-reinforced cement boards (GRC), carbon fiber-reinforced cement boards, calcium silicate boards, gypsum boards, hard boards, lime cream, gypsum plasters, dolomite plasters, blocks, bricks, tiles, fired clay, natural stone, synthetic stone, glass wool, rock wool, and ceramic fibers; and materials based on organic substances such as wood, wood composites, and particle boards.

When porous materials as mentioned above are treated with the organic silicon compounds of the invention as a water-absorption preventing agent, the compounds are typically diluted with water to a concentration of 1 to 50% by weight, especially 3 to 20% by weight. At a concentration of less than 1%, the compound would fail to exert its function and a dilute solution must be applied in a larger amount, taking a longer time for drying. When diluted to a concentration of more than 50%, the resulting solution remains rather viscous and is less impregnable in porous materials, inviting coating spots and discoloration.

When the organic silicon compound of the invention is diluted with water, various auxiliary additives may be added. Exemplary additives are antiseptic agents, mildew-proof agents, termite control agents, carboxymethyl cellulose, polyvinyl alcohol (PVA), water-soluble acrylic resins, SBR latex, and colloidal silica. These optional additives may be used in conventional amounts insofar as the benefits of the invention are not impaired.

Aqueous dilutions of the inventive organic silicon compounds are applied to porous materials by conventional techniques such as roller coating, brush coating and spraying. Dipping is sometimes useful. Subsequent drying can be done, for example, by allowing the coated or impregnated material to stand at room temperature. Sunlight drying and heat drying are also useful.

The organic silicon compound of the invention with which porous material is impregnated undergoes hydrolysis and condensation to form a water repellent and water-absorption preventing layer firmly bound to the porous material. Coating or impregnation of porous materials with the inventive organic silicon compound is effective for solving problems associated with water, for example, leakage of rain water, deterioration of material by acid rain, penetration of stains, salt damages by sea water, freezing in cold areas, and whitening by salt leaching out of material. The inventive organic silicon compound is also useful as an undercoating waterproof primer for various paints and finishers.

EXAMPLE

Examples of the present invention are given below by way of illustration and not by way of limitation. All parts are by weight.

Example 1

10.5 grams (0.04 mol) of decyltrimethoxysilane, 8.8 grams of methanol, 0.8 grams of acetic acid, and 2.2 grams (0.12 mol) of water were mixed and stirred at 25° C. for 1 hour, yielding a clear solution.

A 500-ml four-necked flask equipped with a condenser, thermometer and dropping funnel was charged with 85 grams (0.37 mol calculated as a dimmer) of a methyltrimethoxysilane oligomer and 170 grams of methanol. With stirring, the hydrolyzate of decyltrimethoxysilane was added dropwise to the flask whereupon the contents were stirred at 25° C. for 1 hour. Thereafter, 5.1 grams of acetic acid and 6.7 grams (0.37 mol) of water were admitted into the flask whereupon the contents were stirred at 25° C. for a further 1 hour. To the flask, 17.8 grams (0.08 mol) of N-(2-aminoethyl)-3-aminopropyltrimethoxysilane was added dropwise. The flask was then heated for reaction to the reflux temperature of methanol for 1 hour. Methanol was distilled off by means of an ester adapter until an interior temperature of 110° C. was reached, obtaining a pale yellow clear solution, designated sample No. 1, having a weight average molecular weight of 1,300.

Example 2

21.0 grams (0.08 mol) of decyltrimethoxysilane, 17.6 grams of methanol, 1.6 grams of acetic acid, and 4.4 grams (0.24 mol) of water were mixed and stirred at 25° C. for 1 hour, yielding a clear solution.

A 500-ml four-necked flask equipped with a condenser, thermometer and dropping funnel was charged with 85 grams (0.37 mol calculated as a dimmer) of a methyltrimethoxysilane oligomer and 170 grams of methanol. With stirring, the hydrolyzate of decyltrimethoxysilane was added dropwise to the flask whereupon the contents were stirred at 25° C. for 1 hour. Thereafter, 10.2 grams of acetic acid and 5.8 grams (0.32 mol) of water were admitted into the flask whereupon the contents were stirred at 25° C. for a further 1 hour. To the flask, 17.8 grams (0.08mol) of N-(2-aminoethyl)-3-aminopropyltrimethoxysilane was added dropwise. The flask was then heated for reaction to the reflux temperature of methanol for 1 hour. Methanol was distilled off by means of an ester adapter until an interior temperature of 110° C. was reached, obtaining a pale yellow clear solution, designated sample No. 2, having a weight average molecular weight of 1,500.

Comparative Example 1

8.2 grams (0.04 mol) of hexyltrimethoxysilane, 5.5 grams of methanol, 0.6 grams of acetic acid, and 2.2 grams (0.12 mol) of water were mixed and stirred at 25° C. for 1 hour, yielding a clear solution.

A 500-ml four-necked flask equipped with a condenser, thermometer and dropping funnel was charged with 85 grams (0.37 mol calculated as a dimmer) of a methyltrimethoxysilane oligomer and 170 grams of methanol. With stirring, the hydrolyzate of hexyltrimethoxysilane was added dropwise to the flask whereupon the contents were stirred at 25° C. for 1 hour. Thereafter, 5.1 grams of acetic acid and 6.7 grams (0.37 mol) of water were admitted into the flask whereupon the contents were stirred at 25° C. for a further 1 hour. To the flask, 17.8 grams (0.08 mol) of N-(2-aminoethyl)-3-aminopropyltrimethoxysilane was added dropwise. The flask was then heated for reaction to the reflux temperature of methanol for 1 hour. Methanol was distilled off by means of an ester adapter until an interior temperature of 110° C. was reached, obtaining a pale yellow clear solution, designated sample No. 3, having a weight average molecular weight of 1,000.

Comparative Example 2

6.6 grams (0.04 mol) of propyltrimethoxysilane, 3.0 grams of methanol, 0.4 grams of acetic acid, and 2.2 grams (0.12 mol) of water were mixed and stirred at 25° C. for 1 hour, yielding a clear solution.

A 500-ml four-necked flask equipped with a condenser, thermometer and dropping funnel was charged with 85 grams (0.37 mol calculated as a dimmer) of a methyltrimethoxysilane oligomer and 170 grams of methanol. With stirring, the hydrolyzate of propyltrimethoxysilane was added dropwise to the flask whereupon the contents were stirred at 25° C. for 1 hour. Thereafter, 5.1 grams of acetic acid and 6.7 grams (0.37 mol) of water were admitted into the flask whereupon the contents were stirred at 25° C. for a further 1 hour. To the flask, 17.8 grams (0.08 mol) of N-(2-aminoethyl)-3-aminopropyltrimethoxysilane was added dropwise. The flask was then heated for reaction to the reflux temperature of methanol for 1 hour. Methanol was distilled off by means of an ester adapter until an interior temperature of 110° C. was reached, obtaining a pale yellow clear solution, designated sample No. 4, having a weight average molecular weight of 700.

Comparative Example 3

A 500-ml four-necked flask equipped with an aspirator and thermometer was charged with 136 grams (1.0 mol) of methyltrimethoxysilane, 222.0 grams (1.0 mol) of N-(2-aminoethyl)-3-aminopropyltrimethoxysilane, and 43.2 grams (2.4 mol) of water. While the reaction solution was heated and stirred, stripping was carried out through the aspirator so that the solution might be kept at 60° C., obtaining a pale yellow clear solution, designated sample No. 5, having a weight average molecular weight of 900.

Use Example 1

Test samples were prepared by diluting 20 parts of the water-soluble organic silicon compounds prepared in Examples and Comparative Examples with 80 parts of water as shown in Table 1, dipping mortar pieces in the solutions, curing and thereafter air drying at room temperature for one week. The samples were tested for surface state, water-absorption prevention, penetration depth, and water repellency by the following procedures.

(a) Surface State and Water-absorption Prevention

A JIS mortar specimen of 50×50×25 mm was totally dipped in the organic silicon compound solution for 5 minutes so as to provide a coverage of 100 g/m². The specimen was cured in an atmosphere of RH 50% for 7 days. The surface state of the specimen was visually observed and rated "○" when no wet color was found and "X" when wet color was found.

Subsequently, the specimen was dipped in city water for 28 days. A percent water absorption was calculated according to the following expression.

Water absorption (%)={(weight of mortar after water absorption)−(weight of mortar before water absorption)}/ (weight of mortar before water absorption)×100

(b) Penetration Depth

A specimen dipped and cured as in test (a) was cut into two strips. Water was applied to the cut section so that the cured layer might be easily perceivable. The penetration depth from the surface was measured.

(c) Water Repellency

A water droplet, 0.5 cc, was dropped onto a surface of a specimen dipped and cured as in test (a) and observed for contact angle. The specimen was rated "○" when a large contact angle, indicative of water repellency, was found, "Δ" when an intermediate contact angle was found, and "X" when water was absorbed.

The results are shown in Table 1.

TABLE 1

| Sample No. | Organic silicon compound | Surface state | Water absorption (wt %) | Penetration depth (mm) | Water repellency |
|---|---|---|---|---|---|
| 1 | No.1 | ○ | 1.7 | 3.0 | ○ |
| 2 | No.2 | ○ | 1.2 | 2.5 | ○ |
| 3* | No.3 | ○ | 4.4 | 0.5 | Δ |
| 4* | No.4 | x | 5.9 | 0 | x |
| 5* | No.5 | x | 6.0 | 0.5 | x |

*comparison

Use Example 2

Test samples were prepared by diluting 20 parts of the water-soluble organic silicon compounds prepared in Examples and Comparative Examples with 80 parts of water as shown in Table 2, dipping brick pieces in the solutions, curing and thereafter air drying at room temperature for one week. The samples were tested for surface state, water-absorption prevention, penetration depth, and water repellency by the following procedures.

(a) Surface State and Water-absorption Prevention

A brick specimen of 50×50×25 mm was totally dipped in the organic silicon compound solution for 5 minutes so as to provide a coverage of 100 g/m². The specimen was cured in an atmosphere of RH 50% for 7 days. The surface state of the specimen was visually observed and rated "○" when no wet color was found and "X" when wet color was found.

Subsequently, the specimen was dipped in city water for 28 days. A percent water absorption was calculated according to the following expression.

Water absorption (%)={(weight of brick after water absorption)−(weight of brick before water absorption)}/ (weight of brick before water absorption)×100

(b) Penetration Depth

A specimen dipped and cured as in test (a) was cut into two strips. Water was applied to the cut section so that the cured layer might be easily perceivable. The penetration depth from the surface was measured.

(c) Water Repellency

A water droplet, 0.5 cc, was dropped onto a surface of a specimen dipped and cured as in test (a) and observed for contact angle. The specimen was rated "○" when a large contact angle, indicative of water repellency, was found, "Δ" when an intermediate contact angle was found, and "X" when water was absorbed.

The results are shown in Table 2.

TABLE 2

| Sample No. | Organic silicon compound | Surface state | Water absorption (wt %) | Penetration depth (mm) | Water repellency |
|---|---|---|---|---|---|
| 6 | No.1 | ○ | 0.6 | 7.0 | ○ |
| 7 | No.2 | ○ | 0.5 | 6.5 | ○ |
| 8* | No.3 | ○ | 5.3 | 0.5 | Δ |
| 9* | No.4 | x | 5.6 | 0.5 | x |
| 10* | No.5 | x | 6.0 | 0.5 | x |

*comparison

Use Example 3

Test samples were prepared by diluting 10 parts of the water-soluble organic silicon compounds prepared in Examples and Comparative Examples with 90 parts of water as shown in Table 3, dipping wood pieces in the solutions, curing and thereafter air drying at room temperature for one week. The samples were tested for surface discoloration and water-absorption prevention by the following procedures.

(d) Surface Discoloration and Water-absorption Prevention

A wood (cypress) specimen of 30×30×100 mm was totally dipped in the organic silicon compound solution at room temperature and atmospheric pressure for 24 hours. The specimen was cured at room temperature for 7 days. The surface color (yellowing) of the specimen was visually observed and rated "○" when no discoloring was found, "Δ" for some discoloring, and "X" for discoloring.

Subsequently, the specimen was totally dipped in city water for 24 hours. A percent water absorption was calculated according to the following expression.

Water absorption (%)={(weight of wood after water absorption)−(weight of wood before water absorption)}/ (weight of wood before water absorption)×100

TABLE 3

| Sample No. | Organic silicon compound | Surface discoloring | Water absorption (wt %) |
|---|---|---|---|
| 11 | No.1 | Δ | 10.0 |
| 12 | No.2 | ○ | 9.0 |
| 13* | No.3 | x | 22.0 |
| 14* | No.4 | x | 24.5 |
| 15* | No.5 | x | 26.0 |
| 16* | — | ○ | 30.0 |

*comparison

Note that sample No. 16 is a wood specimen dipped in city water free of an organic silicon compound.

There have been described water-soluble organic silicon compounds which are fully water soluble and shelf stable and which can be used as a water-absorption preventing agent for porous materials simply by diluting with water. Porous materials are coated or impregnated with the compounds so that they are given excellent water repellency and water absorption-preventing effect. The method of the invention ensures preparation of such water-soluble organic silicon compounds.

Japanese Patent Application No. 256893/1995 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. A method for preparing a water-soluble organic silicon compound comprising effecting co-hydrolysis in the presence of an organic or inorganic acid of (A) 1 to 30 parts by weight of an alkyltrialkoxysilane of the following general formula (1):

$$R^1Si(OR^2)_3 \qquad (1)$$

wherein $R^1$ is a hydrocarbon group having 7 to 18 carbon atoms and $R^2$ is an alkyl group having 1 to 4 carbon atoms, or a partial hydrolyzate thereof, (B) 70 to 90 parts by weight of an alkoxy-containing siloxane of the following general formula (2):

$$R^3{}_a(OR^2)_bSiO_{(4-a-b)/2} \qquad (2)$$

wherein $R^2$ is as defined above, $R^3$ is an alkyl group having 1 to 6 carbon atoms, letter a is a positive number of 0.75 to 1.5, b is a positive number of 0.2 to 2, and $0.95<a+b<3.4$, and (C) 1 to 20 parts by weight of an amino-containing alkoxysilane of the following general formula (3):

$$R^4R^5NR^6-SiR^7{}_n(OR^2)_{3-n} \qquad (3)$$

wherein $R^2$ is as defined above, $R^4$ and $R^5$ are independently selected from the group consisting of a hydrogen atom, alkyl and aminoalkyl groups having 1 to 15 carbon atoms, $R^6$ is a divalent hydrocarbon group having 1 to 18 carbon atoms, $R^7$ is an alkyl group having 1 to 4 carbon atoms, and letter n is 0 or 1.

2. The method of claim 1 wherein the co-hydrolysis includes effecting hydrolysis of an alkyltrialkoxysilane of formula (1) or a partial hydrolyzate thereof in the presence of an organic or inorganic acid, mixing the resulting hydrolyzate with an alkoxy-containing siloxane of formula (2), effecting hydrolysis of the mixture in the presence of an organic or inorganic acid, and finally reacting the resulting hydrolyzates with an amino-containing alkoxysilane of formula (3) or a partial hydrolyzate thereof.

3. The method of claim 1 wherein the hydrolysis is carried out in an alcoholic solvent.

4. The method of claim 1 wherein the water-soluble organic silicon compound obtained has a weight average molecular weight of 500 to 5,000.

5. A method of preventing water absorption of a porous material by applying thereto a water-soluble organic silicon compound obtained according to the method of claim 1.

6. An agent for preventing water absorption comprising a water-soluble organic silicon compound obtained according to the method of claim 1.

7. A method of preventing water absorption of a porous material by applying thereto a water-soluble organic silicon compound obtained according to the method of claim 2.

8. An agent for preventing water absorption which comprises a water-soluble organic silicon compound obtained according to the method of claim 2.

9. The method of claim 1, wherein $R^1$ is an alkyl group of 7–18 carbon atoms.

10. The method of claim 1, wherein $R^1$ is a $C_7$–$C_{10}$ alkyl group.

11. The method of claim 1, wherein $R^6$ is an alkylene group of 1–18 carbon atoms.

12. The method of claim 1, wherein there are 5 to 20 parts of component (A), 70 to 80 parts of component (B) and 10 to 20 parts of component (C).

13. The method of claim 1, wherein the organic or inorganic acid is hydrochloric, sulfuric, methanesulfonic, formic, acetic, propionic, citric, oxalic or maleic acid or mixtures thereof.

14. The method of claim 2, wherein the water for hydrolysis of the alkyltrialkoxysilane (A) is added to component (A) in an amount of 1 to 4 mol per mol of (A).

15. The method of claim 2, wherein the acid for hydrolysis of the alkyltrialkoxysilane (A) is provided in an amount of 2 to 40 parts by weight per 100 parts by weight of (A).

16. The method of claim 2, wherein the hydrolysis of the alkyltrialkoxysilane (A) is conducted at a temperature of 10 to 40° C. for 1 to 3 hours.

17. The method of claim 2, wherein the amount of organic or inorganic acid used for hydrolysis of the mixture of the resulting hydrolyzate and the alkoxy-containing siloxane (B) is 2 to 40 parts by weight per 100 parts by weight of (B).

18. The method of claim 2, wherein the amount of water used for hydrolysis of the mixture of the resulting hydrolyzate and the alkoxy-containing siloxane (B) is 0.5 to 1.5 mol per mol of (B).

19. The agent of claim 6, wherein the water-soluble organic silicon compound is diluted with water to a concentration of 1 to 50% by weight.

20. The agent of claim 8, wherein the water-soluble organic silicon compound is diluted with water to a concentration of 1 to 50% by weight.

* * * * *